United States Patent
Kosai et al.

(10) Patent No.: US 12,310,998 B2
(45) Date of Patent: May 27, 2025

(54) THERAPEUTIC PHARMACEUTICAL COMPOSITION FOR BONE AND SOFT TISSUE TUMORS

(71) Applicant: Surv BioPharma Inc., Kagoshima (JP)

(72) Inventors: Ken-ichiro Kosai, Kagoshima (JP); Satoshi Nagano, Kagoshima (JP); Toshitaka Futagawa, Kagoshima (JP)

(73) Assignee: Surv BioPharma Inc., Kagoshima (JP)

( * ) Notice: Subject to any disclaimer, the term of this patent is extended or adjusted under 35 U.S.C. 154(b) by 0 days.

(21) Appl. No.: 18/560,539

(22) PCT Filed: May 18, 2022

(86) PCT No.: PCT/JP2022/020609
§ 371 (c)(1),
(2) Date: Nov. 13, 2023

(87) PCT Pub. No.: WO2022/244792
PCT Pub. Date: Nov. 24, 2022

(65) Prior Publication Data
US 2024/0252561 A1    Aug. 1, 2024

(30) Foreign Application Priority Data

May 19, 2021    (JP) ................. 2021-084823

(51) Int. Cl.
*A61K 35/761*    (2015.01)
*A61P 35/00*    (2006.01)
*C12N 7/00*    (2006.01)

(52) U.S. Cl.
CPC ............ *A61K 35/761* (2013.01); *A61P 35/00* (2018.01); *C12N 7/00* (2013.01); *C12N 2710/10022* (2013.01); *C12N 2710/10032* (2013.01); *C12N 2710/10071* (2013.01)

(58) Field of Classification Search
None
See application file for complete search history.

(56) References Cited

U.S. PATENT DOCUMENTS

| | | |
|---|---|---|
| 2007/0036759 A1 | 2/2007 | Kosai et al. |
| 2009/0181907 A1 | 7/2009 | Kamizono et al. |
| 2021/0008134 A1 | 1/2021 | Kosai et al. |

FOREIGN PATENT DOCUMENTS

| | | |
|---|---|---|
| WO | WO 2005/012536 A1 | 2/2005 |
| WO | WO 2005/115476 A1 | 12/2005 |

OTHER PUBLICATIONS

Japanese Office Action issued May 7, 2024 in corresponding Japanese Patent Application No. 2023-522687 (with English translation), 15 pages.

Zhu, Zeng B., et al., "Incorporating the survivin promoter in an infectivity enhanced CRAd-analysis of oncolysis and anti-tumor effects in vitro and in vivo," International Journal of Oncology, vol. 27 (2005), pp. 237-246.

Zhu, Zeng B., et al., "Targeting Mesothelioma Using an Infectivity Enhanced Survivin-Conditionally Replicative Adenoviruses," Journal of Thoracic Oncology, vol. 1, No. 7, Sep. 2006, pp. 701-711.

Horikawa, Y., et al., "Assessment of an altered E18 promoter on the specificity and potency of triple-regulated conditionally replicating adenoviruses: implications for the generation of ideal m-CRAs," Cancer Gene Therapy, vol. 18 (2011), pp. 724-733.

Ding, M., et al., "Prostate Cancer-Specific and Potent Antitumor Effect of a DD3-Controlled Oncolytic Virus Harboring the PTEN Gene," PLos ONE, vol. 7, Issue 4, Apr. 2012, 11 pages.

Komiya, Setsuro, et al., "Current therapeutic modalities and newly designed gene therapy for refractory sarcomas," Journal of Orthopaedic Science, vol. 24 (2019), pp. 764-769.

Nagano, Satoshi, et al., "Survivin-responsive conditionally replicating adenovirus for patients with advanced sarcoma demonstrated potent and long-term efficacy and high safety in a phase I clinical trial," (Abstract only), Journal of Clinical Oncology, vol. 38, No. 15 Suppl. (2020) , 3 pages.

Kosai, Ken-ichiro, et al., "Phase 1 Study of Potentially "Best-in-Class" Survivin-Responsive Conditionally Replicating Adenovirus for Advanced Sarcoma Actually Demonstrates Potent and Long-Term Efficacy and High Safety." Molecular Therapy, vol. 26, No. 5S1, May 2018, p. 8.

Nagano, Satoshi, et al., "Abstract CT122: Phase I study of potentially "best-in-class" surviving-responsive conditionally replicating adenovirus for advanced sarcoma actually demonstrates potent and long-term efficacy and high safety." (Abstract only), Cancer Research, vol. 78 (13 Suppl), 2018, 4 pages.

International Search Report issued Jul. 26, 2022, in PCT/JP2022/020609 (with English Translation), 4 pages.

Kamizono. J. et al. "Survivin-Responsive Conditionally Replicating Adenovirus Exhibits Cancer-Specific and Efficient Viral Replication". Cancer Res. 2005. vol. 65. No. 12. pp. 5284-5291.

Nagano. S. et al. "An efficient construction of conditionally replicating adenoviruses that target tumor cells with multiple factors". Gene Therapy. 2005. vol. 12. pp. 1385-1393.

Georgi. F. et al. "The Adenovirus Death Protein—a small membrane protein controls cell lysis and disease". FEBS Letters. 2020. vol. 594. pp. 1861-1878.

Murali. V. K. et al. "Adenovirus Death Protein (ADP) Is Required for Lytic Infection of Human Lymphocytes". Journal of Virology. 2014. vol. 88. No. 2. pp. 903-912.

(Continued)

*Primary Examiner* — Robert M Kelly
(74) *Attorney, Agent, or Firm* — Oblon, McClelland, Maier & Neustadt, L.L.P.

(57) ABSTRACT

A method for treating a bone and soft tissue tumor, including administering a conditionally replicating adenovirus having a E1A gene under expression control of a Survivin promoter, to a subject in need thereof. A conditionally replicating adenovirus including a E1A gene under expression control of a Survivin promoter and the conditionally replicating adenovirus is not defective in a E3 region.

18 Claims, 3 Drawing Sheets

(56) References Cited

OTHER PUBLICATIONS

Farrera-Sal. M. et al. "Arming Oncolytic Adenoviruses: Effect of Insertion Site and Splice Acceptor on Transgene Expression and Viral Fitness". Int. J. Mol. Sci. 2020. vol. 21. No. 5158. pp. 1-15.

Suzuki. K. et al. "The presence of the adenovirus E3 region improves the oncolytic potency of conditionally replicative adenoviruses". Clinical Cancer Research. 2002. vol. 8. pp. 3348-3359.

Thanindratarn. P. et al. "Cyclin-dependent kinase 12 (CDK12) in chordoma: prognostic and therapeutic value". European Spine Journal. 2020. vol. 29. pp. 3214-3228.

Fariba Navid et al., "Combination of Gemcitabine and Docetaxel in the Treatment of Children and Young Adults With Refractory Bone Sarcoma", Cancer (2008) vol. 113 (2): pp. 419-425.

Italiano et al., "Advanced chondrosarcomas: role of chemotherapy and survival", Annals of Oncology (2013)24: pp. 2916-2922.

Elizabeth Fox et al., "Phase II Study of Sequential Gemcitabine Followed by Docetaxel for Recurrent Ewing Sarcoma, Osteosarcoma, or Unresectable or Locally Recurrent Chondrosarcoma: Results of Sarcoma Alliance for Research Through Collaboration Study 003", The Oncologist 2012; 17: 321.

Stacchiotti S. et al., "Building a global consensus approach to chordoma: a position paper from the medical and patient community", Lancet Oncol. Feb. 2015; 16 (2): pp. 71-83.

Imai R. et al., "Carbon Ion Radiation Therapy for Unresectable Sacral Chordoma: An Analysis of 188 Cases", Int J Radiation Oncol Biol Phys, 95 (1): pp. 322-327, 2016.

Loic Lebellec. et al., "Molecular targeted therapies in advanced or metastatic chordoma patients: Facts and hypotheses", Critical Reviews in Oncology/Hematology, 95 (2015), pp. 125-131.

Mizuguchi H. et al., "Efficient Construction of a Recombinant Adenovirus Vector by an Improved In Vitro Ligation Method", Human Gene Therapy, 1998, vol. 9, pp. 2577-2583.

Bett A. J. et al., "Packaging Capacity and Stability of Human Adenovirus Type 5 Vectors", Journal of Virology, vol. 67, No. 10, 1993, pp. 5911-5921.

Anonymous, "UMIN Clincal Trials Registry", Jan. 1, 2019. XP893215356.

Kaoru Mitsui et al, "Viral Vector-Based Innovative Approaches to Directly Abolishing Tumorigenic Pluripotent Stem Cells for Safer Regenerative Medicine", Molecular Therapy-Methods & Clinical Development, Jun. 1, 2017, vol. 5, pp. 51-58, XP055394785, DOI: 10.1016/j.omtm.2017.03.002.

Watanabe Maki et al, "Adenovirus Biology, Recombinant Adenovirus, and Adenovirus Usage in Gene Therapy", Viruses, Dec. 14, 2021, vol. 13, No. 1. p. 2502, XP093215385, DOI: 10.3390/v13122502.

Taguchi Satoru et al, "Oncolytic virus therapy in Japan: progress in clincal trials and future prospectives", Japanese Journal of Clinical Oncology, Nov. 20, 2018, vol. 49, No. 3, pp. 201-209, XP093215405, DOI: 10.1093/jjco/hyy170.

Extended European Search Report issued on Apr. 1, 2025, in corresponding EP Application No. 22804703.

THERAPEUTIC PHARMACEUTICAL COMPOSITION FOR BONE AND SOFT TISSUE TUMORS

CROSS REFERENCE TO RELATED APPLICATIONS

This application is a National Stage entry under 35 U.S.C. § 371 of PCT/JP2022/020609, filed on May 18, 2022, and claims priority to Japanese Patent Application No. 2021-084823, filed on May 19, 2021. The entire contents of both are incorporated herein by reference.

TECHNICAL FIELD

The present invention relates to the therapeutic field for a bone and soft tissue tumor.

BACKGROUND ART

The "bone and soft tissue" tumor is a term collectively referring to a "bone" tumor and a "soft tissue" tumor. Malignant bone and soft tissue tumors are classified into a primary bone and soft tissue tumor and a metastatic bone and soft tissue tumor. The primary malignant bone tumor (collectively referring to malignant tumors that develop in the bone) is a rare disease with a frequency of occurrence of 4/1,000,000. As the histological types of the primary malignant bone tumor, osteosarcoma having the highest frequency of occurrence (about 40%), followed by chondrosarcoma and Ewing's sarcoma. Osteosarcoma and Ewing's sarcomamore commonly developed in children and the 10 to 19 years old patients with these tumors respectively occupy 40% and 43% of the total patients. As the prognosis of osteosarcoma, a 5-year (disease-free) survival rate of patients with metastasis-free osteosarcoma of extremity is about 60 to 70% and the overall survival rate thereof is about 70 to 80%. As the prognosis of chondrosarcoma, which is reported to possibly recur even after the passage of 5 or 10 years, the 5-year survival rate thereof is 59%, whereas the 20-year (overall) survival rate is 35%. In the case of Ewing's sarcoma, the 5-year (disease-free) survival rate is 69% and the 5-year (overall) survival rate is 72%. Likewise, prognosis differs depending on the occurrence site. The 5-year (disease-free) survival rate of patients developing a tumor in the distal extremity is 68%, whereas the rate is 61% in the case of a tumor in the proximal extremity and 50% in the case of a tumor in the pelvic.

Osteosarcoma is treated with a standard preoperative chemotherapy such as the administration of doxorubicin or cisplatin, and high-dose methotrexate (MTX) to reduce a tumor size, and thereafter, surgically resected. After the surgery, an adjuvant chemotherapy is recommended based on the histological evaluation of the effect of the preoperative chemotherapy. Although the responses to chemotherapies are mostly positive, it cannot be expected to cure osteosarcoma solely by chemotherapies. Since osteosarcoma that develops in the pelvic and body trunk cannot be resected, symptomatic and life-support treatments are mainly applied. The response rate to chemotherapy is only 29% (Non Patent Literature 1). In addition, chemotherapy cannot be sufficiently applied to the elderly and patients with severe complications. In chemotherapy-ineffective cases and recurrent cases, there are no additional treatment options.

Chondrosarcoma is resistant to both radiation therapy and chemotherapy and only surgically treated. Generally, chemotherapy itself is considered ineffective. There is a chemotherapy to be applied to advanced cases but its effectiveness is low (Non Patent Literature 2). In the cases where wide resection can be made such as a tumor developed in the extremity, complete cure can be attained by amputation/transection. However, in most of cases where wide resection cannot be made such as a tumor developed in the trunk-body, incomplete resection results in repeated recurrence and finally in death. In some cases, the degree of malignancy increases during repeated recurrence and distant metastasis may develop. If a local tumor is surely treated to enable the prevention of local recurrence, vital prognosis can be greatly improved including prevention of distant metastasis. In addition, shrinkage of the local tumor itself brings a great advantage to the patient. because if the size of an unresectable recurrent/metastatic lesion increases, pain and dysfunction develop. If a tumor increases in size and pierces the skin, serious symptoms, such as infection and bleeding, occur. However, presently, there are no treatments for reducing the size of chondrosarcoma without fail. A chondrosarcoma is just a disease having unmet medical need.

For treating Ewing's sarcoma, surgical operation and/or radiation therapy for local control (treatment) and systemic chemotherapy must be used together. As chemotherapy, a multi-drug therapy with vincristine, doxorubicin, ifosfamide and etoposide, is a standard treatment. However, the response rate to chemotherapy is only 35% (Non Patent Literature 3). Particularly, recurrence/metastatic cases after chemotherapy have poor prognosis. There are no recommended chemotherapies whose efficacy in recurrence/metastatic cases has been confirmed. In the case of a spine tumor, there are rare cases where surgical resection is applicable and the prognosis is poorer than tumors in other sites. Radiation therapy is an alternative therapy for unresectable cases but it has a risk of secondary cancer. In this circumstance, the development of a novel therapy has been desired.

Chordoma is a bone tumor having a low degree of malignancy but growing in a locally destructive manner. The rate of occurrence in the sacral bone is the highest (50%). The second highest occurrence is in the skull base (30%) and subsequently in the spine (20%). The median age of onset is 60. The rate of occurrence in the skull base is large in children. Chordoma is mostly treated by surgical resection similar to chondrosarcoma. Local control of recurrent chordoma is difficult and the possibility of long-term survival is low (Non Patent Literature 4). It has been recently reported that heavy particle radiotherapy for chordoma is effective. In the report, the 5-year local control rate by the heavy particle radiotherapy is 77.2% (Non Patent Literature 5). However, re-irradiation to the same site is mostly not applicable, because it may cause damage to healthy organs. Due to the risk, curative irradiation is not applicable in many cases. 30 to 40% of chordoma cases are associated with distant metastasis, which is usually developed after local recurrence. There are no effective chemotherapies for progressive chordoma (the response rate of chemotherapy to chordoma is as low as 0 to 2%). Although clinical trials for molecular-targeted drugs have been reported, the drugs have not yet been approved (Non Patent Literatures 4 and 6). In chordoma, similarly to chondrosarcoma, if local recurrence can be prevented by surely treating a local tumor, vital prognosis can be greatly improved including prevention of distant metastasis as well as shrinkage of the local tumor itself brings a great advantage to the patient. Because if the size of an unresectable recurrent/metastatic lesion increases, pain and dysfunction develop. If a tumor increases in size and pierces the skin, serious symptoms, such as infection and bleeding, occur. Furthermore, in the case of chordoma, the sacrum and cervical spine are favored sites of occurrence. If chordoma presses the spinal cord and the nerve root, neuropathic pain and motor paralysis may cause and suffer the patient. If such symptoms can be reduced even slightly by reducing the size of a tumor, a great advantage would be given to the patient. However, there are presently no therapies for surely reducing the size of chordoma. In other words, chordoma is just a malignant bone tumor with extremely high unmet medical need having no existing therapy.

For bone tumors except osteosarcoma, chondrosarcoma and Ewing's sarcoma, since the number of cases is low, a standard therapy based on evidence has not been established. A therapy is applied based on the decision by a doctor in charge. For example, undifferentiated high-grade pleomorphic sarcoma (so-called MFH) is treated as a highly malignant bone tumor by the same therapy as in osteosarcoma. Bone fibrosarcoma, which is a disease with fewer cases and standard chemotherapy has not been established, is primarily treated by a surgery operation for complete resection. As mentioned above, chemotherapy for many malignant bone tumors including chordoma and chondrosarcoma has not been established as a standard treatment. Although chemotherapy is applied to progress cases, the effectiveness of the chemotherapy is low.

In the meantime, a primary malignant soft-tissue tumor (collectively referring to malignant tumors that develop in the soft tissue) is a rare tumor having an incidence rate of 2 to 3 per 100,000, which is slightly larger than that of a primary malignant bone tumor. As to histological type, malignant fibrous histiocytoma (MFH) was the most common until now, but the use of the term "MFH" has been prohibited since the WHO tissue sarcoma diagnostic criteria were revised in 2013. Currently, liposarcoma, undifferentiated pleomorphic sarcoma (narrowly defined MFH) and leiomyosarcoma commonly appear.

Examples of the primary malignant soft tissue tumors, for which chemotherapy and radiation therapy have been established as standard treatments, are a round cell sarcoma of extraosseous Ewing's sarcoma, and rhabdomyosarcoma alone. Common primary malignant soft tissue tumors such as liposarcoma and undifferentiated pleomorphic sarcoma are primarily treated by a surgical operation. Recently, a molecularly targeted drug, pazopanib targeting a vascular endothelial growth factor (VEGF) has been approved as a drug for a malignant soft tissue tumor. However, the effectiveness of the drug for each histological-type of malignant soft tissue tumors is not yet sufficiently established and treatment options other than this are few up to present.

Non-round cell sarcoma is a soft tissue tumor formed of spindle cells or polygonal cells, such as leiomyosarcoma, malignant fibrous histiocytoma and synovial sarcoma. Non-round cell sarcoma has a considerably higher frequency of occurrence than round cell sarcoma but its sensitivity to chemotherapy is low. The effectiveness of the chemotherapy has not been established. As to a resectable non-progressive case, a surgical operation is a standard therapy in the world. A recent meta-analysis has shown that adjuvant chemotherapy with doxorubicin and ifosfamide is effective. However, as to chemotherapy care must be taken for adverse events. Chemotherapy should be applied in consideration of the age and general condition of the patient; and after providing sufficient explanation about the risks and benefits to the patient.

A survivin-responsive conditionally replicating adenovirus (Surv.m-CRA) refers to an "oncolytic virus" or a "conditionally replicating adenovirus (CRA)", which is proliferated specifically in the malignant tumor cells expressing survivin for the purpose of damaging tumor cells infected with the adenovirus (Patent Literature 1, Non Patent Literature 4). The virus can proliferate in a tumor-specific manner by introducing the Survivin promoter, which is abnormally and highly activated specifically in the tumor cells, into a site upstream of the E1A gene required for the adenovirus proliferation using a genetic recombination technique. At the same time, the virus can also proliferate in a tumor-specific virus manner by a different mechanism by introducing a cytomegalovirus promoter into a site downstream the gene to control the expression of the mutated ElB (defective in the 55 KD coding region). Because of this, the virus is positioned as a next-generation CRA (Non Patent Literature 7, Patent Literature 2).

It has been reported that survivin is not expressed in the normal tissue but strongly expressed in lung cancer, colon cancer, pancreatic cancer, prostate cancer, breast cancer and lymphoma. The present inventors have reported that survivin mRNA is expressed in stomach cancer, colon cancer, liver cancer, cervical cancer and osteosarcoma cell line, and is rarely expressed in fibroblasts and osteoblasts (Non Patent Literature 8). However, it has not yet been reported that the Survivin promoter is highly activated in a tumor-specific manner in malignant bone and soft tissue tumors including chordoma.

CITATION LIST

Patent Literature

Patent Literature 1: International Publication No. WO2005/115476
Patent Literature 2: International Publication No. WO2005/012536

Non Patent Literatures

Non Patent Literature 1: Fariba Navid. et al., CANCER (2008) Vol. 113 (2): 419-425.
Non Patent Literature 2: A. Italiano. et al., Annals of Oncology (2013)24: 2916-2922.
Non Patent Literature 3: Elizabeth Fox. et al., The Oncologist 2012; 17: 321.
Non Patent Literature 4: Stacchiotti S. et al., Lancet Oncol. 2015 February; 16 (2): e71-83.
Non Patent Literature 5: Imai R. et al., Int J Radiation Oncol Biol Phys, 95 (1): 322-327, 2016
Non Patent Literature 6: Loic Lebellec. et al., Hematology 95 (2015)125-131
Non Patent Literature 7: Nagano S. et al., Gene Ther. 12 (18):1385-1393, 2005.
Non Patent Literature 8: Kamizono J et al., Cancer Res 2005, 65: 5284-5291.

SUMMARY OF INVENTION

Technical Problem

A malignant bone and soft tissue tumor tends to have poor prognosis. A therapy for completely treating the tumor has not yet been found. A cancer therapy using a conditionally replicating adenovirus has been reported but a method for effectively treating cancer by the monotherapy has not been found. An object of the present invention is to provide a novel conditionally replicating adenovirus and a novel method for treating a bone and soft tissue tumor by using the adenovirus.

Solution to Problem

The present inventors conducted intensive studies with a view to providing a method for treating a bone and soft tissue tumor. As a result, they found that a pharmaceutical composition for treating the tumor, containing a conditionally replicating adenovirus having the E1A gene under control of a Survivin promoter, as an active ingredient, is effective for the bone and soft tissue tumor; and that the composition has a significant effect and safety over conditionally replicating adenoviruses reported up to present, particularly on recurrent cases to which existing therapies including a standard therapy are not effective. Based on the findings, the present invention was accomplished. They further conducted studies with a view to developing a more effective therapy using a conditionally replicating adenovirus having the E1A gene under control of a Survivin promoter. As a result, they developed an administration method that can enhance the effectiveness of the therapy.

The present inventors further found, different from previous reports, that the tumor-specificity of Surv.m-CRA (Kamizono et al.) having a high tumor-specificity is more improved and a side effect of Surv.m-CRA damaging normal cells can be reduced while maintaining a tumor-cell (specific) cytotoxic effect for tumor cells by maintaining the E3 region of an adenovirus.

According to a first aspect of the present invention, the following [1] to [15] are provided.

[1] A pharmaceutical composition containing a conditionally replicating adenovirus having the E1A gene under expression control of a Survivin promoter, for use in treating a bone and soft tissue tumor (preferably, malignant bone and soft tissue tumor, such as primary malignant bone tumor, metastatic bone tumor, primary malignant soft tissue tumor and metastatic soft tissue tumor), wherein the conditionally replicating adenovirus is not defective in the E3 region.

[2] The pharmaceutical composition according to [1], wherein the bone and soft tissue tumor is a primary bone and soft tissue tumor.

[3] The pharmaceutical composition according to [1], wherein the bone and soft tissue tumor is a recurrent primary bone and soft tissue tumor or a recurrent metastatic bone and soft tissue tumor.

[4] The pharmaceutical composition according to any one of [1] to [3], wherein the bone and soft tissue tumor is a bone tumor.

[5] The pharmaceutical composition according to [4], wherein the bone tumor is chordoma.

[6] The pharmaceutical composition according to [1], wherein a total dosage of the conditionally replicating adenovirus to a subject per dose is $1 \times 10^{10}$ vp to $1 \times 10^{12}$ vp.

[7] The pharmaceutical composition according to [1], which is administered once or repeatedly once every 4 weeks, and preferably 3 to 5 times at a rate of once every 4 weeks.

[8] The pharmaceutical composition according to [1], wherein a dosage volume is varied in accordance with the volume of a tumor to receive administration.

[9] The pharmaceutical composition according to [1], wherein the total dosage of the conditionally replicating adenovirus to a subject per dose is $1 \times 10^{11}$ vp.

[10] The pharmaceutical composition according to [1], wherein if a tumor is present in a plurality of sites, the composition is administered to at most three tumor sites and the dosage is divided into portions in accordance with the volumes of the tumors.

[11] The pharmaceutical composition according to [1], wherein if a tumor at one site has a volume of 30 $cm^3$ or more, the composition is administered only to the site.

[12] The pharmaceutical composition according to [8] or [10], wherein the dosage volume is determined as follows:
  1 mL if the volume of a tumor to receive administration is less than 5 $cm^3$;
  2 mL if the volume of a tumor to receive administration is 5 $cm^3$ or more and less than 9 $cm^3$;
  3 mL if the volume of a tumor to receive administration is 9 $cm^3$ or more and less than 15 $cm^3$;
  5 mL if the volume of a tumor to receive administration is 15 $cm^3$ or more and less than 21 $cm^3$;
  7 mL if the volume of a tumor to receive administration is 21 $cm^3$ or more and less than 30 $cm^3$; and
  10 mL if the volume of a tumor to receive administration is 30 $cm^3$ or more.

For example, if the total dosage of the conditionally replicating adenovirus to a subject per dose is $1 \times 10^{11}$ vp, any dosage volume of the pharmaceutical composition contains $1 \times 10^{11}$ vp of the conditionally replicating adenoviruses; and if the composition is administered to a plurality of tumors, a total of individual dosage volumes contains $1 \times 10^{11}$ vp of conditionally replicating adenoviruses.

[13] A conditionally replicating adenovirus having the E1A gene under expression control of a Survivin promoter, wherein the conditionally replicating adenovirus is not defective in E3 region.

[14] The pharmaceutical composition according to [1] or conditionally replicating adenovirus according to [13], wherein the E1B region of the conditionally replicating adenovirus is E1BΔ55K.

[15] The pharmaceutical composition or conditionally replicating adenovirus according to [14], wherein the E1B region of the conditionally replicating adenovirus is controlled by a promoter different from a promoter controlling the E1A region, for example, a promoter selected from a CMV promoter, an RSV promoter, a CA promoter, an E2F promoter, an EF1A promoter, an EFS promoter, a CAG promoter, a CBh promoter, a CBA promoter, an SFFV promoter, an MSCV promoter, an SV40 promoter, an mPGK promoter, a hPGK promoter, a UBC promoter, a Nanog promoter, an Nes promoter, a Tuba1a promoter, a Camk2a promoter, an SYN1 promoter, a Hb9 promoter, a Th promoter, an NSE promoter, a GFAP promoter, an iba1 promoter, a ProA1 promoter, a hRHO promoter, a hBEST1 promoter, a Prnp promoter, a Cnp promoter, a K14 promoter, a BK5 promoter, an mTyr promoter, a cTnT promoter, an 06MHC promoter, a Myog promoter, an ACTA1 promoter, an MHCK7 promoter, an SM22a promoter, an EnSM22a promoter, a Runx2 promoter, an OC promoter, a Col1a1 promoter, a Col2a1 promoter, an aP2 promoter, an Adipoq promoter, a Tie1 promoter, a Cd144 promoter, a CD68 promoter, a CDllb promoter, an Afp promoter, an Alb promoter, a TBG promoter, an MMTV promoter, a Wap promoter, a HIP promoter, a Pdx1 promoter, an Ins2 promoter, an Hcn4 promoter, an NPHS2 promoter, an SPB promoter, a CD144 promoter, a TERT promoter, a TRE promoter, an FLK-1 promoter, a VEGF promoter, a c-Myc promoter, an SLPI promoter, a PSA promoter and a tyrosinase promoter, and preferably a CMV promoter.

The present invention further provides the following [16] to [20]. The elements defined by [1] to [15] according to the first aspect can apply to the following [16] to [20].

[16] A pharmaceutical composition for treating a recurrent bone and soft tissue tumor, containing a conditionally replicating adenovirus having the E1A gene under expression control of a Survivin promoter, for treating a recurrent bone and soft tissue tumor.

[17] A pharmaceutical composition for treating a bone and soft tissue tumor, containing a conditionally replicating adenovirus having the E1A gene under expression control of a Survivin promoter, wherein the composition is administered once or repeatedly once every 4 weeks, and preferably 3 to 5 times at a rate of once every 4 weeks

[18] A pharmaceutical composition for treating a bone and soft tissue tumor, containing a conditionally replicating adenovirus having the E1A gene under expression control of a Survivin promoter, wherein a dosage volume is varied in accordance with the volume of a tumor.

[19] A pharmaceutical composition for treating a bone and soft tissue tumor, containing a conditionally replicating adenovirus having the E1A gene under expression control of a Survivin promoter, wherein a safe treatment can be made if a total dosage of the conditionally replicating adenovirus to a subject per dose falls within the range of $1 \times 10^{10}$ vp to $1 \times 10^{12}$ vp.

[20] A pharmaceutical composition for treating a bone and soft tissue tumor, containing a conditionally replicating adenovirus having the E1A gene under expression control of a Survivin promoter, wherein the total dosage of the conditionally replicating adenovirus to a subject per dose is $1 \times 10^{11}$ vp.

According to a second aspect of the present invention, the following [1] to [19] are provided.

[1] A method for (safely) treating a bone and soft tissue tumor (preferably, a malignant bone and soft tissue tumor, for example, a primary malignant bone tumor, a metastatic bone tumor, a primary malignant soft tissue tumor, and a metastatic soft tissue tumor), including administering a conditionally replicating adenovirus having the E1A gene under expression control of a Survivin promoter, to a subject.

[2] The method according to [1], wherein the bone and soft tissue tumor is a primary bone and soft tissue tumor.

[3] The method according to [1], wherein the bone and soft tissue tumor is a recurrent primary bone and soft tissue tumor or a recurrent metastatic bone and soft tissue tumor.

[4] The method according to [1], wherein the bone and soft tissue tumor is a bone tumor.

[5] The method according to [4], wherein the bone tumor is chordoma.

[6] The method according to [1], wherein a total dosage of the conditionally replicating adenovirus to a subject per dose is $1 \times 10^{10}$ vp to $1 \times 10^{12}$ vp.

[7] The method according to [1], wherein the conditionally replicating adenovirus is administered once or repeatedly once every 4 weeks, and preferably 3 to 5 times at a rate of once every 4 weeks.

[8] The method according to [1], wherein a dosage volume of the conditionally replicating adenovirus is varied in accordance with the volume of a tumor to receive administration.

[9] The method according to [1], wherein the total dosage of the conditionally replicating adenovirus to a subject per dose is $1 \times 10^{11}$ vp.

[10] The method according to [1], wherein if a tumor is present in a plurality of sites, the conditionally replicating adenovirus is administered to at most 3 tumor sites and the dosage is divided into portions in accordance with the volumes of the tumors.

[11] The method according to [1], wherein if a tumor at one site has a volume of 30 $cm^3$ or more, the conditionally replicating adenovirus is administered only to the site.

[12] The method according to [8] or [10], wherein the dosage volume of a conditionally replicating adenovirus is determined as follows:

1 mL if the volume of a tumor to receive administration is less than 5 $cm^3$;
2 mL if the volume of a tumor to receive administration is 5 $cm^3$ or more and less than 9 $cm^3$;
3 mL if the volume of a tumor to receive administration is 9 $cm^3$ or more and less than 15 $cm^3$;
5 mL if the volume of a tumor to receive administration is 15 $cm^3$ or more and less than 21 $cm^3$;
7 mL if the volume of a tumor to receive administration is 21 $cm^3$ or more and less than 30 $cm^3$; and
10 mL if the volume of a tumor to receive administration is 30 $cm^3$ or more.

For example, if the total dosage of the conditionally replicating adenovirus to a subject per dose is $1 \times 10^{11}$ vp, $1 \times 10^{11}$ vp of the conditionally replicating adenoviruses is administered in any volume of the administration liquid contains; and if the conditionally replicating adenovirus is administered to a plurality of tumors, $1 \times 10^{11}$ vp of conditionally replicating adenoviruses is administered as a total volume of individual administration liquids.

[13] The method according to [1], wherein the conditionally replicating adenovirus is not defective in the E3 region.

[14] The method according to [1], wherein the E1B region of the conditionally replicating adenovirus is E1BΔ55K.

[15] The method according to [1], wherein the E1B region of the conditionally replicating adenovirus is controlled by a promoter different from a promoter (as sets forth in the first aspect) controlling the E1A region.

[16] The method according to [1], wherein the E1B region of the conditionally replicating adenovirus is controlled by the CMV promoter.

According to a third embodiment of the present invention, the following [1] to [15] are provided.

[1] A composition containing a conditionally replicating adenovirus having the E1A gene under expression control of a Survivin promoter, for use in treating a bone and soft tissue tumor (preferably, a malignant bone and soft tissue tumor, for example, primary malignant bone tumor, metastatic bone tumor, primary malignant soft tissue tumor, metastatic soft tissue tumor), wherein the conditionally replicating adenovirus is not defective in the E3 region (maintains the E3 region).

[2] The composition for use according to [1], wherein the bone and soft tissue tumor is a primary bone and soft tissue tumor (for example, primary malignant bone tumor, primary malignant soft tissue tumor).

[3] The composition for use according to [1] or [2], wherein the bone and soft tissue tumor is a recurrent primary bone and soft tissue tumor (for example, primary malignant bone tumor, primary malignant soft tissue tumor) or a recurrent metastatic bone and soft tissue tumor (for example, metastatic bone tumor, metastatic soft tissue tumor).

[4] The composition for use according to any one of [1] to [3], wherein the bone and soft tissue tumor is a bone tumor.

[5] The composition for use according to [4], wherein the bone tumor is chordoma.

[6] The composition for use according to any one of [1] to [5], wherein a total dosage of the conditionally replicating adenovirus to a subject per dose is $1 \times 10^{10}$ vp to $1 \times 10^{12}$ vp.

[7] The composition for use according to any one of [1] to [6], wherein the conditionally replicating adenovirus is administered once or repeatedly once every 4 weeks, and preferably 3 to 5 times at a rate of once every 4 weeks.

[8] The composition for use according to any one of [1] to [7], wherein a dosage volume is varied in accordance with the volume of a tumor to receive administration.

[9] The composition for use according to any one of [1] to [8], wherein the total dosage of the conditionally replicating adenovirus to a subject per dose is $1 \times 10^{11}$ vp.

[10] The composition for use according to any one of [1] to [9], wherein if a tumor is present in a plurality of sites, the composition is administered to tumors of at most three sites and the dosage is divided into portions in accordance with the volumes of the tumors.

[11] The composition for use according to any one of [1] to [9], wherein if a tumor at one site has a volume of 30 cm³ or more, the conditionally replicating adenovirus is administered only to the site.

[12] The composition for use according to any one of [1] to [11], wherein the dosage volume is determined as follows:
1 mL if the volume of a tumor to receive administration is less than 5 cm³;
2 mL if the volume of a tumor to receive administration is 5 cm³ or more and less than 9 cm³;
3 mL if the volume of a tumor to receive administration is 9 cm³ or more and less than 15 cm³;
5 mL if the volume of a tumor to receive administration is 15 cm³ or more and less than 21 cm³;
7 mL if the volume of a tumor to receive administration is 21 cm³ or more and less than 30 cm³; and
10 mL if the volume of a tumor to receive administration is 30 cm³ or more.

For example, if the total dosage of the conditionally replicating adenovirus to a subject per dose is $1 \times 10^{11}$ vp, any volume of the administration liquid of the pharmaceutical composition contains $1 \times 10^{11}$ vp of the conditionally replicating adenoviruses; and if the composition is administered to a plurality of tumors, a total of individual dosage volumes contains $1 \times 10^{11}$ vp of conditionally replicating adenoviruses.

[13] The composition for use according to any one of [1] to [12], wherein the E1B region of the conditionally replicating adenovirus is E1BΔ55K.

[14] The composition for use according to any one of [1] to [13], wherein the E1B region of the conditionally replicating adenovirus is controlled by a promoter different from a promoter (as sets forth in the first aspect) controlling the E1A region.

[15] A conditionally replicating adenovirus according to [14] having the E1A gene under expression control of a Survivin promoter, wherein the adenovirus is not defective in the E3 region; preferably, the E1B region is E1BΔ55K; and (as described in the first aspect) further preferably, the E1B region is controlled by a promoter different from a promoter controlling the E1A region, for example, a CMV promoter.

The present invention further provides the following [16] to [20]. The elements defined by [1] to [15] according to the third aspect can apply to the following [16] to [20].

[16] A composition containing a conditionally replicating adenovirus having the E1A gene under expression control of a Survivin promoter, for use in treating a recurrent bone and soft tissue tumor.

[17] A composition containing a conditionally replicating adenovirus having the E1A gene under expression control of a Survivin promoter, for use in treating a recurrent bone and soft tissue tumor, wherein the composition is administered once or repeatedly once every 4 weeks, and preferably 3 to 5 times at a rate of once every 4 weeks.

[18] A composition containing a conditionally replicating adenovirus having the E1A gene under expression control of a Survivin promoter for treating a bone and soft tissue tumor, wherein the dosage volume is varied in accordance with the volume of a tumor to receive administration.

[19] A composition containing a conditionally replicating adenovirus having the E1A gene under expression control of a Survivin promoter, for use in treating a recurrent bone and soft tissue tumor, wherein a safe treatment can be made if a total dosage of the conditionally replicating adenovirus to a subject per dose falls within the range of $1 \times 10^{10}$ vp to $1 \times 10^{12}$ vp.

[20] A composition containing a conditionally replicating adenovirus having the E1A gene under expression control of a Survivin promoter, for use in treating a bone and soft tissue tumor, wherein the total dosage of the conditionally replicating adenovirus to a subject per dose is $1 \times 10^{11}$ vp.

DESCRIPTION OF EMBODIMENTS

Figure 1:
FIG. 1 The figure shows the therapeutic process of a patient (45 years old, female) having sacral chordoma and treated with a low dose of a drug. The patient developed sacral chordoma in 2007, had a recurrence in 2013 in the right buttock soft tissue, not applicable either chemotherapy or radiation therapy, and was administered with Surv.m-CRA-1 in August of 2016. The middle table shows response evaluations (upper stage) based on the RECIST standard and response evaluations (lower stage) based on the Choi standard from before administration to 114 weeks after administration. The photographs shown in the lowermost part are CT images of a lesion before administration, 12 weeks, 28 weeks and 100 weeks after administration in the order from the left (PR: partial response, SD: stable disease condition).

In an embodiment, the present invention relates to a pharmaceutical composition for treating a bone and soft tissue tumor, containing a conditionally replicating adenovirus having the E1A gene under expression control of a Survivin promoter as an active ingredient.

The "conditionally replicating adenovirus (CRA)" refers to a virus proliferating specific to a tumor to damage the tumor. The "conditionally replicating adenovirus" is also called an oncolytic virus, which is commonly known in the field to which the invention pertains.

In the specification, "having the E1A gene under expression control of a Survivin promoter" means that the Survivin promoter directly binds to a site upstream of the E1A gene so as to control the expression of the E1A gene. For example, the Survivin promoter may bind to a site 10 to 200 bp upstream of the transcription initiation region of the E1A gene. Preferably, the E1B region of conditionally replicating adenovirus is E1BΔ55K. The "E1BΔ55K" refers to a protein obtained by removing a p53 binding region from the adenovirus E1B protein (JAMES R. BISCHOFF et al., SCIENCE 18 Oct. 1996: 373-376), and is also called E1B19K. It is known that the virus having E1BΔ55K can be proliferated in the tumor cells having a deletion of p53 but cannot be proliferated in normal cells having p53.

It is preferable that the E1A region and the E1B region (E1BΔ55K) are controlled by different promoters. Due to this, it is possible to separately control the expression of E1A and the expression of E1BΔ55K (Nagano et al., WO2005/012536). In the specification, such an adenovirus is set forth as "CRA regulated with multiple tumor-specific factors; m-CRA". A promoter controlling the E1B region is not particularly limited as long as it is different from a promoter controlling the E1A region. Examples of the promoter include a CMV promoter, an RSV promoter, a CA promoter, an E2F promoter, an EF1A promoter, an EFS promoter, a CAG promoter, a CBh promoter, a CBA promoter, an SFFV promoter, an MSCV promoter, an SV40 promoter, an mPGK promoter, a hPGK promoter, a UBC promoter, an Nanog promoter, an Nes promoter, a Tuba1a promoter, a Camk2a promoter, an SYN1 promoter, a Hb9 promoter, a Th promoter, an NSE promoter, a GFAP promoter, an iba1 promoter, a ProA1 promoter, a hRHO promoter, a hBEST1 promoter, a Prnp promoter, a Cnp promoter, a K14 promoter, a BK5 promoter, an mTyr promoter, a cTnT promoter, an QMHC promoter, a Myog promoter, an ACTA1 promoter, an MHCK7 promoter, an SM22a promoter, an EnSM22a promoter, a Runx2 promoter, an OC promoter, a Col1a1 promoter, a Col2a1 promoter, an aP2 promoter, an Adipoq promoter, a Tie1 promoter, a Cd144 promoter, a CD68 promoter, a CD11b promoter, an Afp promoter, an A1b promoter, a TBG promoter, an MMTV promoter, a Wap promoter, a HIP promoter, a Pdx1 promoter, an Ins2 promoter, an Hcn4 promoter, an NPHS2 promoter, an SPB promoter, a CD144 promoter, a TERT promoter, a TRE promoter, an FLK-1 promoter, a VEGF promoter, a c-Myc promoter, an SLPI promoter, a PSA promoter, and a tyrosinase promoter.

Examples of the m-CRA include those disclosed in International Publication No. WO2005/115476, or Junichi Kamizono et al., Cancer Res Jun. 15, 2005 (65) (12) 5284-5291. The adenovirus is a m-CRA obtained by replacing an endogenous promoter of the E1A region in the adenovirus genome and an endogenous promoter of the E1B region (preferably, E1BΔ55K) with a Survivin promoter and a CMV promoter, respectively.

The conditionally replicating adenovirus preferably has no insert of an exogenous gene in the E3 region of an adenovirus. In other words, the conditionally replicating adenovirus is a conditionally replicating adenovirus which is not defective in the E3 region (i.e., having the E3 region of a wild-type adenovirus).

Since the E3 region has a region encoding a gene of "Adenovirus Death Protein" inducing tumor cell death, it has been generally considered that an adenovirus having the E3 region has a higher therapeutic effect (Fanny Georgi, et al., FEBS Letters 594 (2020) 1861-1878). However, contrary to the common technical knowledge, the present inventors found that a conditionally replicating adenovirus having the E3 region has a higher tumor-specific cytotoxic effect in vitro than that having no E3 region; and confirmed that the conditionally replicating adenovirus having the E3 region (Surv.m-CRA-1) has a sufficient therapeutic effect and safety in the clinical trials set forth in Examples. In short, since a conditionally replicating adenovirus having the E3 region (not defective in E3 region) maintains a tumor-cell specific cytotoxic effect sufficient to clinically produce a therapeutic effect but drastically reduces a cytotoxic effect non-specific to normal cells, the adenovirus can be a safer and more effective therapeutic drug.

The conditionally replicating adenovirus of the present invention is useful as (a component of) a pharmaceutical composition for treating a bone and soft tissue tumor.

In the specification, the "bone and soft tissue tumor" refers to a tumor formed in the bone and soft tissue (e.g., muscle, fat, nerve, blood vessel). Examples of the bone and soft tissue tumor include osteosarcomas such as conventional osteosarcoma, chondroblastic osteosarcoma, fibroblastic osteosarcoma, osteoblastoma, vascular dilatation osteosarcoma, small cell osteosarcoma, secondary osteosarcoma, parosteal osteosarcoma, periosteal osteosarcoma and high-grade surface osteosarcoma; chondrosarcomas such as conventional chondrosarcoma, dedifferentiated chondrosarcoma, mesenchymal chondrosarcoma, clear cell chondrosarcoma and osteomyxochondrosarcoma; Ewing's sarcoma; high-grade pleomorphic undifferentiated sarcoma (so-called MFH); fibrosarcoma of bone; chordoma; malignant giant cell tumor of bone; angiosarcoma of bone; leiomyosarcoma of bone; and liposarcoman of bone. The "bone and soft tissue tumor" includes a bone tumor and a soft tissue tumor, is preferably, bone tumor and more preferably chordoma.

The "bone and soft tissue tumor" is preferably a malignant bone and soft tissue tumor. The bone and soft tissue tumors are classified into a primary bone and soft tissue tumor group and a metastatic bone and soft tissue tumor group. The "primary bone and soft tissue tumor" refers to a malignant tumor (cancer) derived from the bone and soft tissue itself. The "metastatic bone and soft tissue tumor" refers to a malignant tumor formed in the bone and soft tissue by metastasis of cancer in other organs such as internal organs.

The conditionally replicating adenovirus of the present invention is effective for a recurrent primary bone and soft tissue tumor and a metastatic bone and soft tissue tumor. The "recurrent primary bone and soft tissue tumor" refers to a primary bone and soft tissue tumor, to which a treatment such as radiation therapy and chemotherapy is already applied and/or surgical treatment such as resection is applied, and thereafter exacerbated or becomes metastatic. Also, the "recurrent primary bone and soft tissue tumor"

refers to a metastatic bone and soft tissue tumor, to which a treatment is already applied, and thereafter, exacerbated or becomes metastatic.

The conditionally replicating adenovirus of the present invention may be used in combination with a therapy for a bone and soft tissue tumor commonly known. The therapy for a bone and soft tissue tumor is disclosed in the clinical practice guidelines for soft tissue tumors at the time of filing the application (Japanese Orthopaedic Association (JOA) Clinical Practice Guidelines on the Management of Soft Tissue Tumors), the NCCN guidelines, the ESMO clinical practice guidelines, the EURACAN guidelines, and the guidelines in other countries (e.g., Cancer Chemother Pharmacol. 2016 January; 77 (1): 133-46). For example, a bone and soft tissue tumor is treated by a chemotherapeutic agent such as vincristine, doxorubicin, cyclophosphamide, ifosfamide, etoposide, pazopanib, trabectedin, eribulin or a combination of these.

In another embodiment, the present invention relates to a method for treating a patient with a bone and soft tissue tumor, characterized by administering an effective amount of a conditionally replicating adenovirus having the E1A gene under expression control of a Survivin promoter; a conditionally replicating adenovirus having the E1A gene under expression control of a Survivin promoter for treating a primary bone and soft tissue tumor; or use of a conditionally replicating adenovirus having the E1A gene under expression control of a Survivin promoter for producing a pharmaceutical composition for treating a primary bone and soft tissue tumor. The above conditionally replicating adenovirus is a conditionally replicating adenovirus maintaining a wild-type E3 region and preferably having E1BΔ55K as the E1B region.

For one example, the conditionally replicating adenovirus of the present invention or a pharmaceutical composition containing the conditionally replicating adenovirus as an active ingredient is administered in accordance with an administration schedule: for example, 1 to 10 times, 2 to 8 times, 3 to 5 times, or 4 or 5 times at a rate of once every 4 weeks. Administration is made by injection. Administration to the blood vessel or intratumoral administration may be performed, and intratumoral administration is preferred.

In the case of intratumoral administration, the dosage volume of the pharmaceutical composition of the present invention can be varied in accordance with the tumor volume. For example, the dosage volume of the pharmaceutical composition disclosed herein may be determined as follows:

1 mL if the volume of a tumor to receive administration is less than 5 cm$^3$;
2 mL if the volume of a tumor to receive administration is 5 cm$^3$ or more and less than 9 cm$^3$;
3 mL if the volume of a tumor to receive administration is 9 cm$^3$ or more and less than 15 cm$^3$;
5 mL if the volume of a tumor to receive administration is 15 cm$^3$ or more and less than 21 cm$^3$;
7 mL if the volume of a tumor to receive administration is 21 cm$^3$ or more and less than 30 cm$^3$; and
10 mL if the volume of a tumor to receive administration is 30 cm$^3$ or more.

The virus can be more widely spread within the tumor by varying the dosage volume in accordance with the volume of the tumor.

In the target patient for treatment, if a tumor is present in a plurality of sites, the conditionally replicating adenovirus may be administered, for example, at most three tumor sites (preferably, three large-diameter tumor sites). In this case, the dose can be divided into portions in accordance with the tumor volumes. Alternatively, if the volume of a tumor at one site is 30 cm$^3$ or more, the conditionally replicating adenovirus may be administered only to the site without being divided. In the case of multiple administrations, if the volume of the tumor to which administration is previously made is found to reduce at the time on and after the second administration time, the conditionally replicating adenovirus may be administered to large three tumors of the lesions to be given at the time on and after the second administration time. The large three tumors herein refer to the largest-diameter tumor, the 2nd largest-diameter tumor and the 3rd largest-diameter tumor. Alternatively, in the case of multiple administrations, if the volume of one of the tumors to which administration is previously made is found to reduce in the administration time on and after the second administration, the conditionally replicating adenovirus may be administered to the 4th largest-diameter tumor of the lesions to be given determined in the first administration time. Similarly, if the volumes of two of the tumors to which administration is previously made are found to reduce, the conditionally replicating adenovirus may be administered to the 4th largest-diameter tumor and the 5th largest-diameter tumor of the lesions to be given determined in the first administration time. If the volumes of three of the tumors to which administration is previously made are found to reduce, the conditionally replicating adenovirus may be administered to 4th largest-diameter tumor, the 5th largest-diameter tumor and 6th largest-diameter tumor of the lesions to be given determined in the first administration time.

The dosage of the conditionally replicating adenovirus per dose can be $1\times10^{10}$ vp to $1\times10^{12}$ vp, and preferably, $1\times10^{11}$ vp. The conditionally replicating adenovirus may be administered once or repeatedly in a plurality of times. The total dosage can be $1\times10^{10}$ vp to $1\times10^{12}$ vp, and is preferably, $1\times10^{11}$ to $5\times10^{11}$ vp or $3\times10^{11}$ to $5\times10^{11}$ vp.

The dosage form of the pharmaceutical composition of the present invention is not particularly limited as long as it is suitable for administration to a tumor site. The pharmaceutical composition may contain pharmacologically acceptable carriers and additives. Examples of the carriers and additives include a solvent, a solubilizer, a suspending agent, an emulsifier, a tonicity agent, a stabilizer, a soothing agent, a preservative, an antioxidant and a buffer.

Examples of the solvent include purified water, physiological saline, and phosphate buffer.

Examples of the solubilizer include polyethylene glycol, propylene glycol, trehalose, benzyl benzoate, ethanol, sodium carbonate, sodium citrate, sodium salicylate, and sodium acetate.

Examples of the suspending agent or emulsifier include sodium lauryl sulfate, gum Arabic, gelatin, lecithin, glyceryl monostearate, polyvinyl alcohol, polyvinylpyrrolidone, cellulose such as carboxymethylcellulose sodium, polysorbates, and polyoxyethylene hydrogenated castor oil.

Examples of the tonicity agent include sodium chloride, potassium chloride, a saccharide, glycerin, and urea.

Examples of the stabilizer include polyethylene glycol, dextran sodium sulfate and amino acids.

Examples of the soothing agent include glucose, calcium gluconate, and procaine hydrochloride.

Examples of the preservative include paraoxybenzoate, chlorobutanol, benzyl alcohol, phenethyl alcohol, dehydroacetic acid, and sorbic acid.

Examples of the antioxidant include water-soluble antioxidants such as ascorbic acid, cysteine hydrochloride, sodium bisulfate, sodium metabisulfite, and sodium sulfite;

fat-soluble antioxidants such as ascorbyl palmitate, butylated hydroxyanisole (BHA), butylated hydroxytoluene (BHT), lecithin, propyl gallate, α-tocopherol; and metal chelating agents such as citric acid, ethylene diamine tetra acetic acid (EDTA), sorbitol, tartaric acid, and phosphoric acid.

The pharmaceutical composition of the present invention can be a preparation for injection containing the conditionally replicating adenovirus in, for example, a glycerin-containing tris-buffered saline buffer (containing 2.5% (v/v) glycerin, 25 mM NaCl, 20 mM Tris, pH 8.0). The amount of the conditionally replicating adenovirus included can be appropriately selected depending on the purpose and dosage regimen, and is preferably, $1 \times 10^{11}$ vp/mL.

EXAMPLES

Now, Examples will be shown to illustrate the present invention in detail but the present invention is not limited to these examples. Note that, all documents cited in the specification are incorporated in their entirety by reference.

Example 1

The medicinal product (Surv.m-CRA-1) used herein contains m-CRA type 5 which was prepared by modifying the E1 region such that the E1A gene is expressed under the control of the Survivin promoter and the E1B19K gene is expressed under the control of the CMV promoter, as an active ingredient. The adenovirus has m-CRA, which is obtained by removing endogenous promoters in E1A and E1B regions required for viral proliferation from the type 5 adenovirus genome, as a basic backbone and has no therapeutic gene. Since the medicinal product contains an adenovirus having the Survivin promoter (Survpr), which was introduced into a site from which the endogenous E1A promoter was deleted (removed) and the CMV promoter (CMVpr), which was introduced into a site from which the endogenous E1B promoter was deleted (removed) by a recombination technique, the adenovirus of the medicinal product selectively proliferates in tumor cells having survivin activated. In contrast, proliferation of the adenovirus in normal cells low in survivin activity is suppressed. Further, Surv.m-CRA-1 has E3.

The final formulation of the drug of the invention was designed as an injectable preparation. Viruses (prepared in a concentration of $1 \times 10^{11}$ vp/mL) are contained at a rate of 0.6 mL per vial of a preparation. The base of the preparation is a GTS buffer consisting of 25 mM NaCl containing 2.5% glycerin (v/v) and 20 mM Tris, pH8.0.

<Eligibility of Subject>

Patients who satisfy all of the following selection criteria and none of the exclusion criteria were determined as eligible and registered.

(Inclusion Criteria)

1) Histologically diagnosed as any one of the following tumors
   primary malignant bone tumor
   metastatic bone tumor
   primary malignant soft tissue tumor
   metastatic soft tissue tumor 2) At the time of registration, 4 weeks or more have passed since the standard treatment if it was applied as a pretreatment 3) Not a subject for a standard treatment commonly recognized and possibly providing life extension and symptom relief 4) having a (tumor) lesion whose minor axis, major axis and height can be measured and to which an investigational product can be administered.

5) The age of a patient at the time of providing informed consent is 10 or more and less than 85 years old.

6) ECOG PS is 0 to 2.

7) expected to live for 3 months or more.

8) having major organ functions (Latest medical data within two weeks before registration)
   hemoglobin ≥8 g/μL
   leucocyte count ≥2,000/μL
   platelet count ≥70,000/μL
   AST (GOT) ≤100 U/L
   ALT (GPT) ≤100 U/L
   total bilirubin ≤1.5 mg/μL
   serum creatinine ≤2.0 mg/μL 9) In the case of a male, one of the following requirements is satisfied.
   azoospermia
   after surgical contraception such as vasectomy.
   already agreed on the prevention of pregnancy by appropriately using condoms or practicing asceticism in the period from the time of providing informed consent to the disappearance of the investigational product, Surv.m-CRA-1 administered from the body.
   The female partner is in a postmenopausal state for more than 1 year or after surgery such as bilateral oophorectomy, or already agreed on prevention of pregnancy by oral contraceptives (contraceptive pill) or intrauterine device (pessary) in the period from the time of providing informed consent to the disappearance of the investigational product, Surv.m-CRA-1 administered from the body.

10) In the case of a female, one of the following requirements is satisfied.
   In a postmenopausal state for more than one year
   After surgical contraception such as bilateral oophorectomy
   already agreed on the prevention of pregnancy by oral contraceptives (contraceptive pill) or intrauterine device (pessary) in the period from the time of providing informed consent to the disappearance of the investigational product, Surv.m-CRA-1 administered from the body.
   The male partner is azoospermia or after surgical contraception such as vasectomy; or already agreed on prevention of pregnancy by appropriately using condoms in the period from the time of providing informed consent to the disappearance of the investigational product, Surv.m-CRA-1 administered from the body.

11) already obtained written informed consent on participation in the clinical test from a subject oneself or a legal representative.

(Exclusion Criteria)

1) having one of the following complications.
   serious heart disease, respiratory disease, digestive disorder, liver disease
   poorly controlled diabetes
   infection that requires ongoing treatment 2) having a history of allergy to penicillin or a pig/cow (including milk).

3) having a disease that requires systemic administration of an immunosuppressant or a steroid (use of a steroid for preventing allergy to a contrast agent is acceptable. If used, about a week interval must be set until the administration of an investigational product and measure is presumably taken for preventing infection).

4) having active double cancer (basal cell carcinoma, carcinoma endoepidermale, superficial bladder cancer, or malignant tumor from which no metastasis or recurrence occurred for more than 5 years is not ineligible)

5) having uncontrolled primary-disease-associated fever/pain 6) a pregnant female, a breastfeeding female, and a premenopausal female or a female within a year of menopause being positive pregnancy test 7) taking an unapproved drug within 4 weeks before providing informed consent.

8) Other females who are determined as inappropriate to participate in the clinical study by an investigator/subinvestigator.

A phase-I study with ascending doses for open-label (Surv.m.CRA-1-001 study) was carried out to evaluate safety/tolerability and preliminary effectiveness of Surv.m-.CRA-1 for a progressive solid cancer (primary malignant bone tumor, metastatic bone tumor, primary malignant soft tissue tumor, metastatic soft tissue tumor) by a single administration to a local site of a tumor. A low dose ($1\times10^{10}$ viral particle hereinafter referred to as "vp"), a medium dose ($1\times10^{11}$ vp) and a high dose ($1\times10^{12}$ vp) of Surv.m-CRA-1 were each administered to 3-eligible subject each described above.

As the tumor site to receive administration, a single site was selected from anatomical positions, based on the following standards. It does not matter if the site is a primary lesion or a metastatic lesion. If 2 or more tumor sites are present, a site to receive administration is selected in consideration of which one is technically easier to administer.

1) A tumor is large in size and to which administration is technically easily made
2) A site not adjacent to major blood vessel and thoracic cavity
3) A site not presumed to be responsible for symptoms such as pain.

Based on a tumor image evaluation finding of a subject at the time of registration, a tumor volume was calculated in accordance with the following formula (rounded down to the second decimal place).

<Calculation of Tumor Volume>

Tumor volume ($cm^3$) = Minor-axis diameter (cm) × Major-axis diameter (cm) × Height (cm) × 1/2

The liquid volume of a medicinal product to be administered to a single lesion is determined as follows: if a tumor volume is 33.3 $cm^3$ or larger in a low-dose cohort, a medium-dose cohort and a high-dose cohort, the medicinal product is diluted so as to be 10 mL and administered. In a low-dose cohort and a medium-dose cohort, if a tumor volume is 3.4 $cm^3$ or less, the medicinal product was administered without dilution; if the tumor volume is 3.5 $cm^3$ to 33.3 $cm^3$ or less, the medicinal product was diluted so as to become 30% of the tumor volume and then administered. In a high-dose cohort, if the tumor volume is 33.3 $cm^3$ or less, a whole amount of the medicinal product was administered without dilution.

In a treatment room, the dosage volume for a single-lesion to receive administration was administered uniformly within the same tumor by changing the direction of a needle tip so as to distribute 5 to 10 sites, under direct visual guidance, X-ray fluoroscopy, CT guidance, or ultrasound guidance.

(Results)

The therapeutic effects of subjects in the phase-I study are shown in Table 1. Of the subjects, a patient (45 years old, female) with sacral chordoma of a low-dose cohort is a case that sacral chordoma metastasized to the liver and lung 6 years after the onset and has a recurrence in the right buttock soft tissue. A chemotherapeutic agent and radiation therapy had no effect and the recurrent tumor was not able to resect. The medicinal product of the invention can achieve a partial response (PR) only by a single administration even in the recurrence case (non-response case by either a chemotherapeutic agent or radiation therapy). In particular, the therapeutic effect and safety were both extraordinarily excellent. In clinical trials for conditionally replicating adenoviruses so far performed, despite repeated administration, it is not reported that a therapeutic effect is obtained at such a low dose. In clinical trials of conditionally replicating adenoviruses, it is not reported that a therapeutic effect was obtained over 2 years or more after administration. The course of treatment is shown in FIG. 1.

Figure 2:
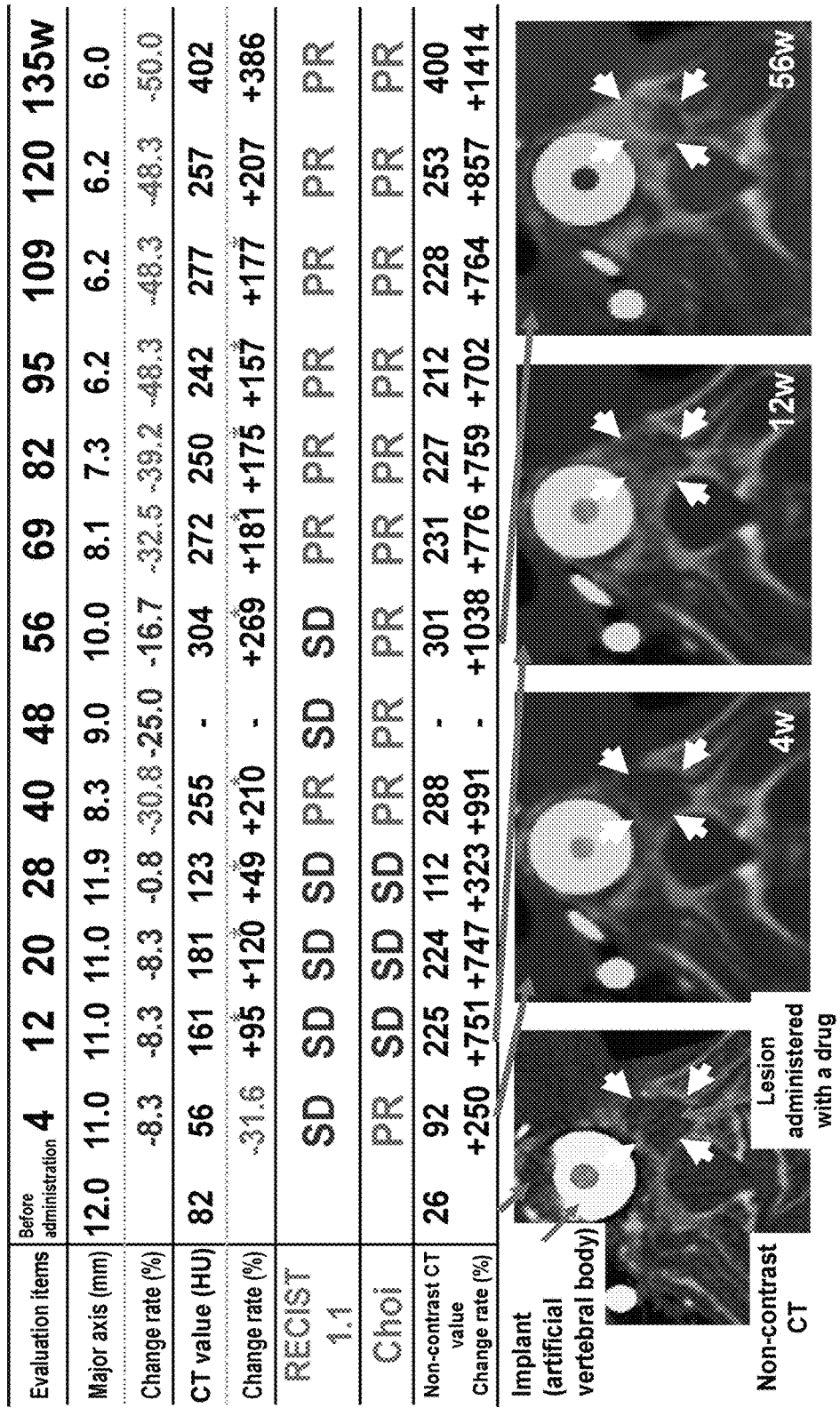
FIG. 2 The figure shows the therapeutic process of a patient (61 years old, male) having thoracic chordoma and treated with a low dose of a drug. The patient had a resection surgery of thoracic chordoma from the right mediastinum in 2006 and the 4th recurrence in the adjacent vertebral body (seventh thoracic spine) in 2017. Since a standard treatment was not effective, Surv.m-CRA-1 was administered. The middle table shows the therapeutic process from before administration to 135 weeks after administration. The table shows the major-axis diameter (mm) and a change rate thereof (%), CT value (HU) and a change rate thereof (%), response evaluations based on the RECIST standard, response evaluations based on the Choi standard, non-contrast-enhanced CT value and a change rate thereof (%) in the order from the top. The photographs shown in the lowermost part are CT images of a lesion before administration, 4 weeks, 12 weeks and 56 weeks after administration in the order from the left (PR: partial response, SD: stable disease condition).

In the case of a patient with thoracic chordoma (61 years old, male) in a low-dose cohort, 11 years after a thoracic chordoma was surgically resected from the right mediastinum, the patient had a 4-th time recurrence in the adjacent vertebral body. This is a case that no effect was produced by a standard treatment. The medicinal product of the present invention was able to achieve PR in such a recurrence case. It should be noted that a therapeutic effect was produced 4 weeks after a treatment and further bone remodeling was observed 12 weeks later. Bone remodeling is a phenomenon of regeneration of bone induced for the first time after a bone tumor disappears. The phenomenon clinically demonstrates a high therapeutic effect. This is a case of a tumor formed within the bone. Even if the tumor leads to cell death, the site where the tumor has been formed cannot be completely filled up by regeneration of bone. Because of this, it is impossible to evaluate a reduction effect on a tumor based on the RECIST, which evaluates tumor diameters. In this sense, it is estimated that a further dramatic therapeutic effect might be obtained. Further, in the Choi, in which evaluation was made by contrast-enhanced CT, the CT value increases. In short, an extremely satisfactory result where bone modeling (regenerative healing) significantly occurs, was shown. In consideration of these results comprehensively, the patient is the case actually obtaining an almost complete response, that is, a strong therapeutic effect. As set forth in the first case, in the clinical trials so far reported, despite the repeated administration of conditionally replicating adenoviruses, it is not reported that a therapeutic effect was observed at such a low dose. From this, the above excellent results obtained at a single administration in the clinical trial are extremely prominent. In clinical trials for conditionally replicating adenoviruses, a case where a therapeutic effect was obtained over 135 weeks (2 years and 7 months (or more)) after administration, was not reported. This is a drastic therapeutic effect. The course of treatment is shown in FIG. 2.

Table 1 summarizes the therapeutic effects of 9 cases in total tested in the clinical trial. The therapeutic effects were evaluated with reference to tumor reduction effects based on the Choi standard and the RECIST standard. PD is progressive disease, SD is a stable disease and PR is a partial response. Safety (adverse event and side effect) was analyzed for all adverse events identified from the day of administration of an investigational product to the end of the observation period. The adverse events were evaluated using the Common Terminology Criteria for Adverse Events (CT- CAE) ver.4.0 translated in Japanese and edited by the Japanese clinical oncology group (JCOG) (CTCAE ver.4.0).

In a single administration low-dose cohort (1/100 dose of the maximum dose at which no therapeutic effect was obtained even if it is repeatedly administered by competing technology in the world), a long-term/persistent tumor therapeutic effect (tumor shrinkage progresses in 2 years or more and decreases by half) was found. An innovative therapeutic action/effect: 6/9 cases in all dose cohorts being effective (PR or more), was obtained in the clinical trial. Such a high efficacy has not been reported in the conditionally replicating adenovirus clinical trials carried out in the world, to date (listed in Table 2). Thus, it was demonstrated that the drug of the invention has a performance that greatly exceeds the competing technology.

study. No variation in laboratory test values and vital signs clinically concerned were observed except for the abnormalities reported as adverse events.

As a whole, no variation in adenovirus in blood, adenovirus excretion (saliva, urine), anti-adenovirus antibody titer, cytokine (level), and 12-lead electrocardiogram clinically concerned were observed in any one of the cohorts. An increase in cytokine level is minor. It is considered that the minor increase in the cytokine level is collateral evidence supporting that excessive immune response to viral infection is not induced.

Patients complained of mild symptoms such as temporal fever but no serious symptoms. From this, it was demonstrated that the drug is extremely safe. As set forth in the above, Surv.m-CRA-1, even though it has E3, maintains a

TABLE 1

| Patient # | Dose (viral load) | Type of cancer | Target lesion | Therapeutic effect Choi (RECIST) | Safety (serious adverse effect) |
|---|---|---|---|---|---|
| 1 | Low-dose | Chordoma | Soft tissue | PR (PR) | High (none) |
| 2 | ($1 \times 10^{10}$) | Chordoma | Thoracic vertebra | PR (PR) | High (none) |
| 3 |  | Epithelioid sarcoma | Soft tissue | PR (SD) | High (none) |
| 4 | Middle-dose | Liposarcoma | Soft tissue | SD (SD) | High (none) |
| 5 | ($1 \times 10^{11}$) | Myxofibrosarcoma | Soft tissue | PR (PD) | High (none) |
| 6 |  | Rectal cancer | Sacral bone | SD (SD) | High (none) |
| 7 | High-dose | Myxofibrosarcoma | Soft tissue | PR (SD) | High (none) |
| 8 | ($1 \times 10^{12}$) | Uterus cancer | Pubic bone | PR (SD) | High (none) |
| 9 |  | Liposarcoma | Soft tissue | PD (SD) | High (none) |

The medicinal product of the invention administered has no dose-dependent tendency to safety. No significant problems were not recognized. As a serious adverse event, Grade-4 reduction in lymphocyte count was observed in a single case. A patient in this case recovered without symptoms. Reduction in lymphocyte count is commonly observed in oncolytic viruses and a temporary event that possibly occurs in amplification of the recombinant virus, and reported in past clinical trials for a conditionally replicating adenovirus. This occurs in a different mechanism from myelosuppression (extremely significant side effect) by conventional chemotherapy (anticancer drug). The number of lymphocytes in the peripheral blood is presumed to reduce by temporarily recruiting lymphocytes to a tumor and/or lymph node in accordance with viral proliferation/cell lysis within a tumor (the action mechanism of the medicinal product of the invention). Since this is not myelosuppression, a reduction in lymphocyte count is recovered early. This phenomenon, in some sense, is deemed to be a ground for demonstrating that the medicinal product of the invention steadily acts. There were no subjects who died within 28 days from the administration of an investigational product. Note that, there were no adverse events and DLT (dose-limiting toxicity) that led to the cancellation of the clinical strong therapeutic effect on tumor cells, whereas non-specific viral proliferation in normal cells is suppressed. From this, it was demonstrated that a highly safe adenovirus, even though it has E3 region, is successfully constructed.

The viral load in the body fluid after administration of the virus was measured. The results are shown in Table 2. In a single case of the low-dose cohort, the saliva was virus-positive on the day of administration (Day 1 alone) but negative in the blood and urine. In the other cases, all of the blood, saliva and urine were virus-negative. In the medium-dose cohort, the 2-case blood samples were virus-positive up to 7 days later (Day 8), one of the cases was virus-positive in the saliva up to 7 days later (Day 8), the other case was virus-positive up to 21 days later (Day 22) but on and after 14 days (on and after Day 1), the viral load was as low as 20 copies/$\mu$L or less. In the high-dose cohort, all 3-case blood samples were virus-positive up to 7 days later (Day 8); 2-case saliva samples were virus-positive up to 7 days later (Day 8); all 3-case urine samples were virus-negative. Although subjects became temporarily virus-positive after administration of an investigational product but became virus-negative by the end of the study treatment/evaluation period (Day 29).

TABLE 2

| | | | Process of viral excretion load (in blood, urine and saliva) after treatment | | | | | | | | | |
|---|---|---|---|---|---|---|---|---|---|---|---|---|
| | | | Before | After administration | | | | | | | | |
| | Type of cancer | Tissue | administration | 3H | Day 1 | Day 2 | Day 7 | Day 14 | Day 21 | Day 22 | Day 23 | Day 28 |
| S-01 (Low dose) | Chordoma | Blood | – | – | – | – | – | – | – | | |
| | | Saliva/ Urine | –/– | 20/– | –/– | –/– | –/– | –/– | | | |
| S-02 (Low dose) | Chordoma | Blood | – | – | – | – | – | – | – | | |
| | | Saliva/ Urine | –/– | –/– | –/– | –/– | –/– | –/– | | | |

TABLE 2-continued

Process of viral excretion load (in blood, urine and saliva) after treatment

| | Type of cancer | Tissue | Before administration | 3H | Day 1 | Day 2 | Day 7 | Day 14 | Day 21 | Day 22 | Day 23 | Day 28 |
|---|---|---|---|---|---|---|---|---|---|---|---|---|
| S-03 (Low dose) | Epithelioid sarcoma | Blood Saliva/ Urine | – –/– | – –/– | – –/– | – –/– | – –/– | – –/– | – –/– | | | |
| S-04 (Middle dose) | Liposarcoma | Blood Saliva/ Urine | – –/– | 21 –/– | – –/– | 88 –/– | 74 –/– | – 14/– | – –/– | | | |
| S-05 (Middle dose) | Myxofibrosarcoma | Blood Saliva/ Urine | – –/– | – –/– | – –/– | – –/– | – –/– | – –/– | – –/– | | | |
| S-06 (Middle dose) | Metastasis of rectal cancer to sacral bone | Blood Saliva/ Urine | – –/– | – 320/– | – 80/40 | – –/– | 18 20,000/18 | – 15/– | – 13/* | –/* | –/* | |
| S-07 (High dose) | Myxofibrosarcoma | Blood Saliva/ Urine | – –/– | – –/– | 11 36/– | – –/– | 22 134/– | – –/– | – | | | |
| 5-08 (High dose) | Metastasis of uterus cancer to pubic bone | Blood Saliva/ Urine | – –/– | 28 534/– | – 42/– | 383 –/– | 94 –/– | – –/– | – | | | |
| S-09 (High dose) | Liposarcoma | Blood Saliva/ Urine | – –/– | 127 174/– | 10 31/– | 19 –/– | 23 766/– | – –/– | – | | | |

Dose (VP/mL) Viral (Surv.m-CRA-1) load
Low (1 × $10^{10}$) Numerical value: copies/μL
Middle (1 × $10^{11}$)  –: < 10 copies/μL
High (1 × $10^{12}$)   *: Not performed since negative value was confirmed Effectiveness was as follows: at the end of the study treatment/evaluation period (Day 29), local response (effectiveness) was observed in two cases of the low-dose cohort, in a single case of the middle-dose cohort and two cases in the high-dose cohort. In the two cases (primary malignant bone tumor: chordoma) of the low-dose cohort, the local response was maintained from Month 9 to 24 (2 years) after initiation of the observation (in one of the two cases, maintained up to the maximum observation period: 2 years and 7 months). From the above, it was found that the (drug) product of the invention has extremely high safety without any problem in tolerability and provides a greater therapeutic effect (tumor reduction effect) over (the products using) conditionally replicating adenoviruses already reported. The results of clinical trials for the conditionally replicating adenovirus already reported and Surv.m-CRA-1 are shown in comparison in the following Table 3.

TABLE 3

| | | | Therapeutic effect Choi(RECIST) | | | |
|---|---|---|---|---|---|---|
| Subject | Investigational product | Dose | PD | SD | PR | Document |
| Gliocytoma | ONYX-015 | 1 × $10^7$ – 1 × $10^{10}$ pfu | 23 | 1 | — | Mol Ther, 2004 |
| Solid cancer | Telomelysin | 1 × $10^{10}$ – 1 × $10^{12}$ vp | 3 | 11 | 1 | Mol Ther, 2010 |
| Hepatobiliary cancer | ONYX-015 | 6 × $10^9$ – 3 × $10^{10}$ pfu | 1 | 12 | 1 | Clin Cancer Res. 2003 |
| Bone and soft tissue tumor | Surv.m-CRA-1 | 1 × $10^{10}$ – 1 × $10^{12}$ vp | 1 | 2 | 6 | The present invention | pfu: Plaque-forming unit
vp: Viral particles

In cohort 3 (high dose) of the phase I study of Surv.m-CRA-1, 1×$10^{12}$ vp of the investigational product was administered and the safety of the product was confirmed. The virus was detected in the body fluid up to Day 7 after administration of the investigational product in almost all cases. In one case of cohort 2 (medium dose: 1×$10^{11}$ vp), the virus was detected in the saliva at longest up to Day 21. In contrast, there were no cases of exhibiting a symptom such as upper respiratory inflammation during the period when the virus was detected in the body fluid. From the above, it was demonstrated that the virus administered disappears from the body fluid 4 weeks after administration of an investigational product and thus, a risk by re-administration is the same as or close to that by the initial administration. From this, it was suggested that the treatment with Surv.m-CRA-1 is suitably made in accordance with a dose-cycling schedule designed so as to administer Surv.m-CRA-1 once every 4 weeks. If the frequency of administration was set as 5 times, it is possible to determine 1×$10^{11}$ vp as a single administration dose, with the result that the total dosage (1×$10^{11}$ vp×5 times=5×$10^{11}$ vp) does not exceed the dosage of cohort 3 of Surv.m-CRA-1 phase I study (high dose: 1×$10^{12}$ vp) and a therapeutic effect can be expected.

It is known that as tumor diameter of bone tumor increases, the risk of pathological fracture increases (Mirel's score: evaluation of pathological fracture at the tumor diameter) and the tumor diameter is used for determining whether surgical operation is appropriate or not. It has been reported that the total volume (Total Tumor Volume) of a primary lesion and metastasis lesion (e.g., lymph node metastasis) is inversely correlated with the prognosis in various types of cancers. Also in osteosarcoma, the total volume of multiple lung metastatic cancers is reported to be a poor prognostic factor. It is expected to reduce the total tumor volume of a patient by treating tumors in descending order from the tumor with a large tumor diameter. Thus, in consideration of the possibility of starting administration from a tumor lesion with a large tumor diameter, the lesion to be treated is selected. The larger the number of target lesions to receive administration, the smaller the dose per lesion and the larger the patient's load. In consideration of this, at most three sites are conceived to be a lesion to receive administration. If the volume of a tumor first to be treated is as large as 30 cm³ or more, and the dose is divided into 2 or more portions, the dose per tumor can be reduced (in phase-I test of Surv.m-CRA-1, a drug was administered so as to cover 30% of a tumor volume as a target). For this reason, administration was made to only one portion.

In this study, the tumor lesion to which an investigational product can be administered refers to a lesion satisfying all of the following conditions:

a main part is bone or soft tissue (metastatic lesion of bone tumor)

injection can be made from the surface of a body into a tumor not a lesion of the lymph node the minimum diameter of a tumor is 10 mm or more the entire tumor is not a cystic lesion.

The liquid volume of a medicinal product to a single (tumor) lesion is determined by calculating the volume of a tumor to receive administration and determining the dosage volume in accordance with the following standard. If dilution is required, dilution is made with saline in accordance with the dosage volume.

Tumor Volume and the Dosage Volume (after Dilution)

| Tumor volume (cm³) | Administration liquid volume (mL) |
|---|---|
| less than 5 | 1 |
| 5 or more and less than 9 | 2 |
| 9 or more and less than 15 | 3 |
| 15 or more and less than 21 | 5 |
| 21 or more and less than 30 | 7 |
| 30 or more | 10 |

If there are a plurality of lesions that can be administered, the dosage volume was calculated based on the total of tumor volumes and in accordance with the above standard. At most three sites of tumors can be administered in every administration time. When administration is made to a plurality of tumors, the dosage volume is divided in accordance with the tumor volumes. The total dosage is determined as $1 \times 10^{11}$ vp. Note that if the volume of a single tumor is 30 cm³ or more, administration is made only the single tumor and administration to another tumor is not performed. If a plurality of lesions that can be administered are present, target lesions are selected based on the following standards by the investigator or a sub-investigator.

The Tumor Diameter is Large

The approach can be made from the surface of a body

Administration can be safely made without the presence of an important nerve and a blood vessel in the neighborhood.

Based on a tumor image evaluation finding of a subject at the time of registration, a tumor volume was calculated in accordance with the following formula (rounded down to the second decimal place).

<Calculation of Tumor Volume>

Tumor volume (cm³) = Minor-axis diameter (cm) ×
Major-axis diameter (cm) × Height (cm) × 1/2

Example 2

Surv.m-CRA-1 was prepared by an improved method based on the m-CRA preparation technology (Patent Literature 2, Non Patent Literature 7) as follows. The structure of Surv.m-CRA-1 has not been reported. First, pSurv.E1A-CMV.19K plasmid was prepared by inserting, to a vector plasmid (P1 plasmid: Replication-controllable plasmid) containing a proliferation control unit, a mouse Survivin promoter (−173 to −19) upstream of E1A, and a CMV promoter upstream of E1BΔ55K in accordance with the method disclosed in Patent Literature 2. Next, the pSurv.E1A-CMV.19K plasmid was digested with restriction enzyme I-Ceul, and then a restriction enzyme PI-Seel, and a DNA sequence (fragment) having a Survivin promoter/E1A/CMV promoter/E1BΔ55K in the order from the upstream was isolated and purified. In the meantime, a fragment of 342-3523 bp was deleted from the sequence of human adenovirus type 5 containing the E1 region. To the site, I-Ceul and PI-Seel recognition sequences were provided (inserted) in order to sub-clone a gene of P1 plasmid. In the meantime, the adenovirus genome plasmid pAd.HM3 (provided by Dr. Mark A. Kay, Stanford University) having the E3 region was digested with restriction enzyme I-Ceul, and then, a restriction enzyme PI-Seel. In each of the steps, purification was made with phenol/chloroform and followed by ethanol precipitation. The DNA fragment of the Survivin promoter/E1A/CMV promoter/E1BΔ55K was inserted into the pAd.HM3 site treated with I-Ceul/PI-Seel by use of T4DNA ligase to obtain conditionally replicating adenoviral vector plasmid, pAd.HM4-Surv.E1A-CMV.19K. Then, 293 cells were transfected with the plasmid pAd.HM4-Surv.E1A-CMV.19K. The virus plaque that emerged was extracted, amplified and purified to obtain Surv.m-CRA-1, which is a "m-CRA having the E1A gene whose expression is controlled by the Survivin promoter, E1BΔ55K whose expression is controlled by the CMV promoter and E3 region".

Example 3

Malignant tumor cells, i.e., liver cancer cell line HepG2 and normal cells, i.e., fibroblasts WI-38, were each infected in vitro with Surv.m-CRA-1 with individual given multiplicity of infections (MOI). On Day 3 and Day 5 after infection, cell viability was evaluated by WST-8 (Nacalai Tesque Inc., catalog number 07553-44). For comparison of properties, E3 region-defective Surv.m-CRA (E3 is absent), which is a "m-CRA having the E1A gene whose expression is controlled by the Survivin promoter, E1BΔ55K whose expression is controlled by the CMV promoter and defective in the E3 region", and a non-replicating adenovirus, Ad.dE1.3 serving as a control for evaluating "death by virus proliferation" were used in experiments performed in the same conditions as comparative experiments. The conditionally replicating adenovirus rapidly proliferates in a malignant tumor, thereby producing a cytotoxic effect. The MOI of malignant tumor HepG2 was 0.3, 1 and 3. In contrast, the level of cytotoxic effect of viral proliferation on normal cells WI-38 in any one of the groups is low. To clearly find the difference between the groups, MOI was 1, 3 and 10, each of which is three times as large as MOI of HepG2.

Figure 3:
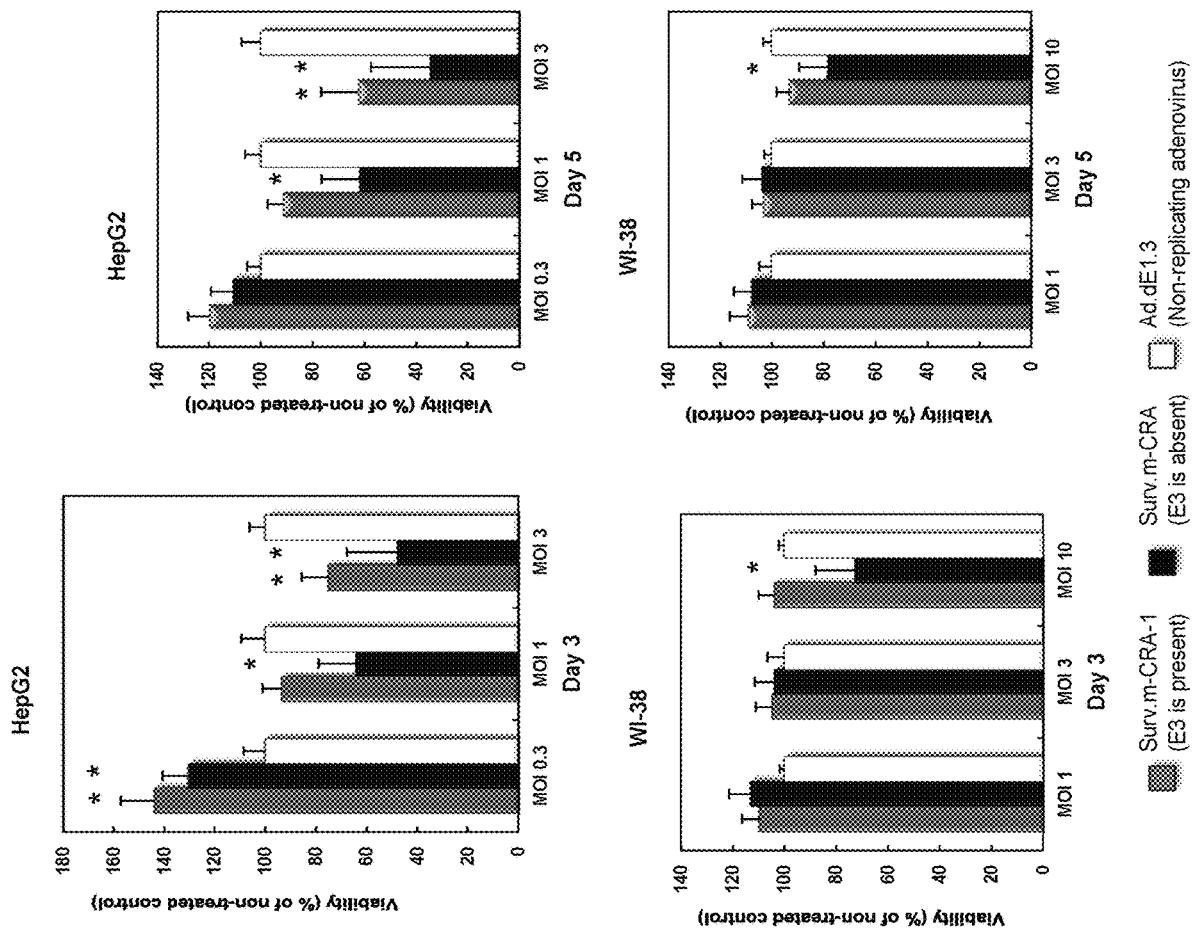
FIG. 3 The figure shows graphs showing the cell viabilities of liver cancer cell line (HepG2) and normal fibroblasts (WI-38) infected with Surv.m-CRA-1 in vitro. The vertical axis shows the ratios (%) of viable cell counts in the cases of Surv.m-CRA-1 (E3 is present) and Surv.m-CRA (E3 is absent) in the same conditions (the same MOI and days) to the viable cell counts (regarded as 100%) of the control, Ad.dE1.3 in individual conditions. The horizontal axis shows the multiplicity of infection (MOI). Reference symbol * indicates statistically significant (P<0.05) to a control.

The 3 groups were compared each MOI and each Day (day after infection). The results are shown in FIG. 3. In individual conditions, the viable cell count of control Ad.dE1.3 was regarded as 100%. The viable cell counts of Surv.m-CRA-1 (E3 is present) and Surv.m-CRA (E3 is absent) were compared in the same conditions (each MOI and Day) and expressed in percentages based on the viable cell count of control Ad.dE1.3. In FIG. 3, the vertical axes of the graphs represent the viability (%) "of cells for comparing 3 groups in the same condition (MOI and Day)" and not the viability of cells for comparison in different MOIs or different Days. In all groups, N=5. An average value and a standard error are also shown in FIG. 3. The statistical significance between the 2 groups in the same condition (each MOI and Day) was calculated by the Student t-test. $P<0.05$ indicates a significant difference. If Surv.m-CRA-1 (E3 is present) and Surv.m-CRA (E3 is absent) each had a significant difference compared to the control Ad.dE1.3, reference symbol * was attached on the bars of them.

It was confirmed that a cytotoxic effect by virus proliferation is produced on malignant tumor cell line HepG2 in the experimental conditions at an MOI of 1 or more. A significant cytotoxic effect by virus proliferation was observed only in Surv.m-CRA (E3 is absent) at an MOI of 1 and observed in both Surv.m-CRA (E3 is absent) and Surv.m-CRA-1 (E3 is present) at an MOI of 3. In short, it is shown that finally the same therapeutic effect can be obtained. In contrast, in normal cells, WI-38, a cytotoxic effect was not observed at any one of the MOIs on Day 3 and Day 5 in Surv.m-CRA-1 (E3 is present). However, in Surv.m-CRA (E3 is absent), a significant cytotoxic effect was observed only at MOI 10 on both Day 3 and Day 5. In short, in Surv.m-CRA (E3 is absent), significant cell death was not induced just like in normal cells WI-38 at an MOI of 3, at which significant cell death is induced in tumor cells HepG2. These two types of survivin-responsive m-CRAs both have a tumor-specific cytotoxic effect, that is, an excellent and distinct performance as a cancer drug but Surv.m-CRA-1 (E3 is present) is further excellent in tumor specificity (safety).

An in vitro experimental system in which a long-term (several ten days, month, year) therapeutic effect having a clinical significance in vivo (human patient) can be completely accurately evaluated and reflected, and an animal model by which the detailed differences can be accurately evaluated, are not present. However, the following scientific conclusion can be sufficiently obtained by the in vitro practicable experimental system of the present invention. That is, a conditionally replicating adenovirus whose proliferation is controlled by the Survivin promoter induces a sufficient tumor cell death and to a tumor specificity (safety). In the respect that Surv.m-CRA-1 (E3 is present) does not damage normal cells, further higher safety (normal cells are not damaged in the in vitro experimental system) is provided. From this, it can be said that Surv.m-CRA-1 (E3 is present) is a further excellent conditionally replicating adenovirus. In view of the therapeutic effect on a tumor, Surv.m-CRA-1 (E3 is present) has a lower cytotoxicity than Surv.m-CRA (E3 is absent) in some in vitro experimental conditions (it is important that the finding is completely contrary to the theory established in the art). However, when Surv.m-CRA-1 (E3 is present) is actually used in clinical sites as a therapeutic drug for a long term (neither several hours nor a few days as in vitro) to provide a clinically beneficial therapeutic effect to a patient in an appropriate amount, Surv.m-CRA-1 (E3 is present) brings a sufficiently strong therapeutic effect equivalent to Surv.m-CRA (E3 is absent). This is consistent with the results that a strong (exceeding conventional conditionally replicating adenoviruses) therapeutic effect and extreme safety (having no serious side effects) were obtained in the clinical trial for a bone and soft tissue malignant tumor of human patients, as shown in Example 1. In short, the technology (technical idea) of the invention, which was found to exceed prior art from a scientific point of view, for the first time, in Example 2 of the present invention, is simultaneously demonstrated for the first time in the human clinical trial in Example 1 of the present invention. Thus, Surv.m-CRA-1 of the present invention is the first conditionally replicating adenovirus greatly exceeding conventional conditionally replicating adenoviruses in performances of both therapeutic effect and safety and having a potential as a cancer drug by itself.

Example 4

Repeat-Dose Study
[Case 1]

The course of treatment of a patient (60 years old, male) having sacral recurrent chordoma with Surv.m-CRA-1 is shown. The patient developed a sacral chordoma in 2014 and started to receive particle beam therapy. In 2019, metastasis to the left kidney was found and nephrectomy was performed. December in 2020, an increase in sacral chordoma was found and administration of Surv.m-CRA-1 was started in May, 2021. The patient satisfies the inclusion criteria shown in Example 1 and does not satisfy the exclusion criteria shown in Example 1. Since the tumor volume was 315 cm$^3$ (30 cm$^3$ or more), the dose ($1\times10^{11}$ vp) of Surv.m-CRA-1 was divided into 9 portions and a total 5 times (total 5×1 every 4 weeks).

Table 4 shows the response evaluations of the administration site (sacrum) based on the RECIST standard and the Choi standard before administration to 32 weeks after administration and the response evaluations of the non-administration site (right iliac wing) based on the RECIST standard before administration to 32 weeks after administration.

TABLE 4

|  | Before administration | 4 w | 12 w | 20 w | 32 w |
|---|---|---|---|---|---|
| Administration site (sacral bone) | | | | | |
| RECIST 1.1 | | | | | |
| Major axis (mm) | 110 | 110 | 110 | 109 | 107 |
| Change rate (%) | | 0.0 | 0.0 | −0.9 | −2.7 |
| Evaluation | | SD | SD | SD | SD |
| Choi | | | | | |
| CT value (HU) | 36.9 | 36.4 | 35.0 | 38.7 | 36.0 |
| Change rate (%) | | −1.4 | −5.1 | 5.1 | −2.4 |
| Evaluation | | SD | SD | SD | SD |
| Non-administration site (right wing of Ilium) | | | | | |
| RECIST 1.1 | | | | | |
| Major axis (mm) | 14 | 17 | 22 | 25 | 27 |
| Change rate (%) | | 21.4 | 57.1 | 78.5 | 92.8 |
| Evaluation | | SD* | PD | PD | PD |

SD: Stable disease,
PD: Progressive disease

As shown in Table 4, a tumor increased at the non-administration site, whereas, a lesion was suppressed and tumor volume decreased at the administration site. The tumor was significantly large but the SD effect was found at a time point of the $8^{th}$ month (32 weeks) after initiation of administration. No adverse events were observed during administration.

[Case 2]

The course of treatment of a patient having recurrent sacral chordoma (73 years old, male) with Surv.m-CRA-1 is shown. The patient developed sacral chordoma in 2016 and a tumor (S3 level) was resected. In 2018, heavy ion radiation therapy (twice) was carried out. In October, 2020, right gastrocnemius muscle metastasis was resected. In 2021, 3 courses of chemotherapy (ADR) were applied. In 2021, a left femoral trochanteric pathologic fracture occurred. In October 2021, tumor growth (recurrent sacral chordoma) in the perineum and sacrum subcutaneous portion was found. In November 2021, the administration of Surv.m-CRA-1 was started. The patient satisfies the inclusion criteria shown in Example 1 and does not satisfy the exclusion criteria shown in Example 1.

The volume of the tumor in the perineum was 22.8 cm³ and the volume of the tumor in the sacrum subcutaneous was 14.95 cm³. From the 1st to 3rd administration times, $5 \times 10^{11}$ vp of Surv.m-CRA-1 was divided as follows and administered. After the 3rd administration time, the dose of Surv.m-CRA-1 was adjusted to $3.5 \times 10^{11}$ vp (7 ml) in accordance with the volume of the tumor reduced in size and the 4th and 5th administrations were carried out.

Administration was carried out every 4 weeks.

|  | 1-3 times | 4 and 5 times |
|---|---|---|
| Perineum: | 7 ml, 4 sites | 5 ml, 3 sites |
| Sacrum subcutaneous portion: | 3 ml, 2 sites | 2 ml, 1 site by injection |

Table 5 shows the response evaluations of the administration sites (perineum, sacrum subcutaneous portion) based on the RECIST standard and the Choi standard before administration to 140 days after administration and the response evaluations of non-administration sites (left rectum, right rectum, in the left gluteus muscle, right ilium) based on the RECIST standard before administration to 84 days after administration.

TABLE 5

|  | Before administration | Day 28 | Day 84 |
|---|---|---|---|
| Administration site (perineum, sacrum subcutaneous) | | | |
| RECIST (MRI) | | | |
| Sum of Major axes (mm) | 86 | 84 | 81 |
| Change rate (%) | | −2.3 | −5.8 |
| Evaluation | | SD | SD |
| Choi (CT) | | | |
| Perineum | | | |
| CT value (HU) | 31 | 37 | 25 |
| Change rate (%) | | 19.3 | −16.7 |
| Evaluation | | PD | PR |
| sacrum subcutaneous | | | |
| CT value (HU) | 36 | 32 | 25 |
| Change rate (%) | | −11.1 | −30.5 |
| Evaluation | | SD | PR |
| Non-administration site (left rectum, right rectum, in the left gluteus muscle, right ilium) | | | |
| RECIST (MRI) | | | |
| Sum of Major axes (mm) | 221 | 230 | 242 |
| Change rate (%) | | 4 | 9.5 |
| Evaluation | | SD | SD |

PR: Partial response,
SD: Stable disease,
PD: Progressive disease

As shown in Table 5, a tumor increased at the non-administration sites, whereas a lesion was suppressed at administration sites. An SD effect at the major axis (RECIST) and a PR effect based on the Choi standard (contrast effect) were confirmed. The volume of a tumor was found to distinguishably reduce. No adverse events except a decrease in lymphocytes (750/μl) were confirmed during administration.

As set forth in the above, the safety and effectiveness of Surv.m-CRA-1 were demonstrated even in the repeated dose (studies). A safer and more effective treatment can be made by controlling the dosage volume in accordance with variation of tumor volume, as performed in Case 2.

The invention claimed is:

1. A pharmaceutical composition for treating a bone and soft tissue tumor, comprising:
   a conditionally replicating adenovirus having an E1A gene under expression control of a Survivin promoter; and
   a pharmacologically acceptable carrier,
   wherein the conditionally replicating adenovirus is not defective in an E3 region, and
   wherein an E1B region of the conditionally replicating adenovirus is E1BΔ55K.

2. The pharmaceutical composition according to claim 1, wherein the E1B region of the conditionally replicating adenovirus is controlled by a promoter different from a promoter controlling the E1A region.

3. The pharmaceutical composition of claim 1, wherein the pharmacologically acceptable carrier comprises at least one solvent selected from the group consisting of purified water, physiological saline, and phosphate buffer.

4. The pharmaceutical composition of claim 1, wherein the pharmacologically acceptable carrier comprises at least one solubilizer selected from the group consisting of polyethylene glycol, propylene glycol, trehalose, benzyl benzoate, ethanol, sodium carbonate, sodium citrate, sodium salicylate, and sodium acetate.

5. The pharmaceutical composition of claim 1, wherein the pharmacologically acceptable carrier comprises at least one suspending agent or emulsifier selected from the group consisting of sodium lauryl sulfate, gum arabic, gelatin, lecithin, glyceryl monostearate, polyvinyl alcohol, polyvinylpyrrolidone, cellulose, carboxymethylcellulose sodium, a polysorbate, and polyoxyethylene hydrogenated castor oil.

6. The pharmaceutical composition of claim 1, wherein the pharmacologically acceptable carrier comprises at least one tonicity agent selected from the group consisting of sodium chloride, potassium chloride, a saccharide, glycerin, and urea.

7. The pharmaceutical composition of claim 1, wherein the pharmacologically acceptable carrier comprises at least one stabilizer selected from the group consisting of polyethylene glycol, dextran sodium sulfate, and amino acids.

8. The pharmaceutical composition of claim 1, wherein the pharmacologically acceptable carrier comprises at least one soothing agent selected from the group consisting of glucose, calcium gluconate, and procaine hydrochloride.

9. The pharmaceutical composition of claim 1, wherein the pharmacologically acceptable carrier comprises at least one preservative selected from the group consisting of paraoxybenzoate, chlorobutanol, benzyl alcohol, phenethyl alcohol, dehydroacetic acid, and sorbic acid.

10. The pharmaceutical composition of claim 1, wherein the pharmacologically acceptable carrier comprises at least one water-soluble antioxidant selected from the group consisting of ascorbic acid, cysteine hydrochloride, sodium bisulfate, sodium metabisulfite, and sodium sulfite.

11. The pharmaceutical composition of claim 1, wherein the pharmacologically acceptable carrier comprises at least one fat-soluble antioxidant selected from the group consisting of ascorbyl palmitate, butylated hydroxyanisole, butylated hydroxytoluene, lecithin, propyl gallate, and α-tocopherol.

12. The pharmaceutical composition of claim 1, wherein the pharmacologically acceptable carrier comprises at least one metal chelating agent selected from the group consisting of citric acid, ethylene diamine tetra acetic acid, sorbitol, tartaric acid, and phosphoric acid.

13. A pharmaceutical composition for treating a bone and soft tissue tumor, comprising:
 a conditionally replicating adenovirus having an E1A gene under expression control of a Survivin promoter; and
 a pharmacologically acceptable carrier,
 wherein the conditionally replicating adenovirus is not defective in an E3 region, and
 wherein an E1B region is E1BΔ55K and is controlled by a CMV promoter.

14. The pharmaceutical composition of claim 13, wherein the pharmacologically acceptable carrier comprises at least one solvent selected from the group consisting of purified water, physiological saline, and phosphate buffer.

15. The pharmaceutical composition of claim 13, wherein the pharmacologically acceptable carrier comprises at least one solubilizer selected from the group consisting of polyethylene glycol, propylene glycol, trehalose, benzyl benzoate, ethanol, sodium carbonate, sodium citrate, sodium salicylate, and sodium acetate.

16. The pharmaceutical composition of claim 13, wherein the pharmacologically acceptable carrier comprises at least one suspending agent or emulsifier selected from the group consisting of sodium lauryl sulfate, gum arabic, gelatin, lecithin, glyceryl monostearate, polyvinyl alcohol, polyvinylpyrrolidone, cellulose, carboxymethylcellulose sodium, a polysorbate, and polyoxyethylene hydrogenated castor oil.

17. The pharmaceutical composition of claim 13, wherein the pharmacologically acceptable carrier comprises at least one tonicity agent selected from the group consisting of sodium chloride, potassium chloride, a saccharide, glycerin, and urea.

18. A conditionally replicating adenovirus having the E1A gene under expression control of a Survivin promoter, wherein the conditionally replicating adenovirus is not defective in an E3 region, and
 wherein an E1B region is E1BΔ55K and is controlled by a CMV promoter.

* * * * *